United States Patent [19]
Russell

[11] Patent Number: 5,244,562
[45] Date of Patent: Sep. 14, 1993

[54] USE OF TEMPLATED POLYMERS FOR ANALYTE-ACTIVATED MICROELECTRONIC SWITCHING DEVICES

[75] Inventor: Dale D. Russell, Boise, Id.

[73] Assignee: Hewlett-Packard Company, Palo Alto, Calif.

[21] Appl. No.: 738,719

[22] Filed: Jul. 31, 1991

[51] Int. Cl.$^5$ .......................................... G01N 27/26
[52] U.S. Cl. ................................. 204/418; 204/416; 204/403; 435/817
[58] Field of Search ................. 204/416, 418, 403; 435/817

[56] References Cited

U.S. PATENT DOCUMENTS 4,818,661  4/1989  Taylor et al. .................. 205/135
5,151,168  8/1992  Gilton et al. .................. 205/135

Primary Examiner—John Niebling
Assistant Examiner—Bruce F. Bell

[57] ABSTRACT

Switching devices (10) comprise a micro-electrode (12 or 16a') coated with a templated polymer (14). For example, the template molecule is glucose and the bulk polymer is a thiophene/boronic acid-substituted thiophene copolymer. The switch is activated or inactivated by the concentration of glucose in a solution (38) contacting the coated micro-electrode. Advantageously, the dimensions of the switch may be very small, $10^{-6}$ or less.

6 Claims, 3 Drawing Sheets

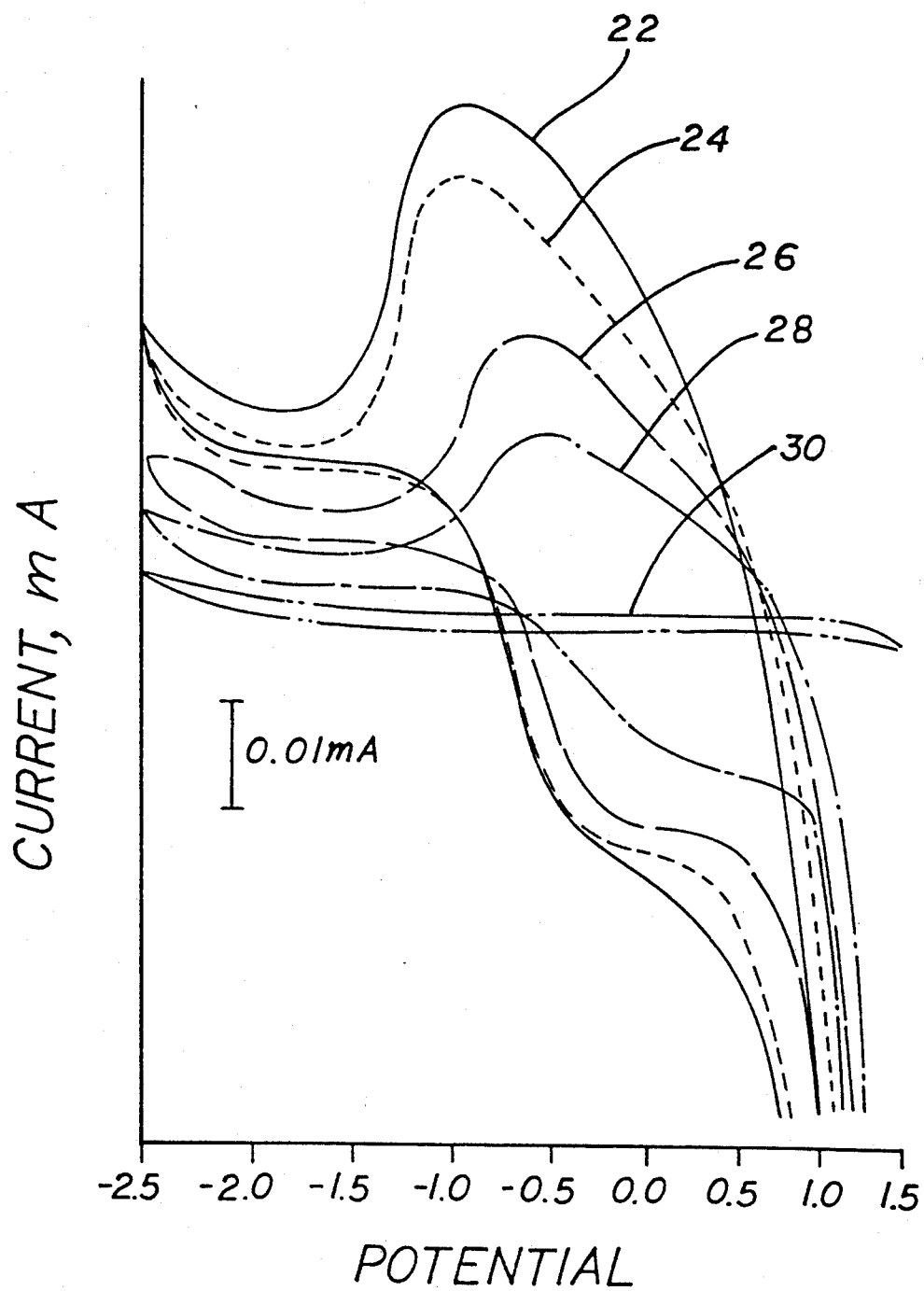

USE OF TEMPLATED POLYMERS FOR ANALYTE-ACTIVATED MICROELECTRONIC SWITCHING DEVICES

TECHNICAL FIELD

The present invention relates to microelectronic switching devices, and, more particularly, to polymers adapted to coact with specific reagents to provide a switching action.

BACKGROUND ART

Polymers can be built around a variety of different kinds of molecules. The chosen molecule becomes a template which, when removed, leaves a vacancy in the bulk polymer which is sterically and electronically selective for the template molecule. This binding site behaves like the binding site of an enzyme.

These vacancies can be filled again by reaction with the templating molecule. The resulting changes in the electronic properties of the bulk polymer may be correlated to the concentration of the template molecule in the test environment.

The prior art of which Applicant is aware may be divided into three categories: modification of electrode surfaces with the application of various polymeric materials; the templating of polymers to achieve molecular recognition; and devices for the purpose of monitoring blood or solution glucose concentrations.

The literature is replete with examples of electrodes modified with various polymeric materials. Examples of representative publications include: G. Caple et al, "Semiconducting Copolymeric Polythiophene Films", *Croatia Chimica Acta*, Vol. 60 (No. 3), pp. 565–568 (1987); L. Laguren-Davidson et al, "Steric Effects on the Controlled Potential Electro-Oxidation of 3-Methyl Thiophene and Thiophene Oligomers and the Properties of Their Polymer Films", *Journal of the Electrochemical Society*, Vol. 135 (No. 6), pp. 1406–1414 (1988); B. L. Wheeler et al, "Electrochemical Amine Sensors Using Carboxylate Functionalized Polythiophene Films", *Journal of the Electrochemical Society*, Vol. 136 (No. 9), pp. 2769–2770 (1989); and E. W. Tsai, "Electrochemistry of Some β-Substituted Polythiophenes", *Journal of the Electrochemical Society*, Vol. 136 (No. 12), 3683–3689 (1989).

Examples of representative publications relating to templated polymers for molecular recognition include: G. Wulff, "Molecular Recognition in Polymers Prepared by Imprinting with Templates", ACS Symposium Series, *Polymeric Reagents and Catalysts*, W. T. Ford, ed., Washington, D.C., Vol. 308, pp. 186–230 (1986); G. Wulff et al, "Enzyme Analogue-Built Polymers", *Makromolecular Chemie*, Vol. 178, pp. 2799–2816 (1977); K. J. Shea et al, "Template Synthesis of Macromolecules. Selective Functionalization of an Organic Polymer", *Journal of Organic Chemistry*, Vol. 43 (No. 21), pp. 4253–4255 (1978); G. Wulff et al, "Molecular Recognition through the Exact Placement of Functional Groups on Rigid Matrices via a Template Approach", *Journal of the American Chemical Society*, Vol. 108 (No. 5), pp. 1089–1091 (1986); G. Wulff et al, "Enzyme-Analogue Built Polymers and Their Use for the Resolution of Racemates", *Tetrahedron Letters*, No. 44, pp. 4329–4332 (1973); and K. J. Shea et al, "Template Synthesis of Macromolecules. Synthesis and Chemistry of Functionalized Macroporous Polydivinylbenzene", *Journal of the American Chemical Society*, Vol. 102 (No. 9), pp. 3149–3155 (1980).

Almost without exception, devices intended for implant into a human for in vivo determination of glucose are based on the use of enzyme, glucose oxidase. A few, such as the following paper, are based on direct electrochemical detection of the glucose at relatively high potentials, physiologically speaking, e.g., 1 volt: S. J. Yao et al, "Low-Potential Electrochemical Redox Sensors", U.S. Pat. No. 4,805,624, issued Feb. 21, 1989.

A need remains for providing selective molecular recognition systems that act as switches, preferably at low potentials where use in the human body is concerned. One way of addressing this need would be the use of templated polymeric materials, as disclosed and claimed herein.

DISCLOSURE OF INVENTION

In accordance with the invention, switching devices are provided, which comprise a micro-electrode coated with a templated polymer. In one embodiment of the invention, the template molecule is glucose and the bulk polymer includes a thiophene/boronic acid-substituted thiophene copolymer. The switch is activated or inactivated by the concentration of glucose in a solution contacting the coated micro-electrode.

Advantageously, the dimensions of the switch may be very small, $10^{-6}$ m or less.

BRIEF DESCRIPTION OF THE DRAWINGS

FIG. 3a, on coordinates of current and voltage, depicts the switching behavior of thiophene/boronic acid-substituted thiophene copolymer in various concentrations of glucose;

BEST MODES FOR CARRYING OUT THE INVENTION

A switch comprising a micro-electrode coated with a templated polymer is now described. In one preferred embodiment, the template molecule is glucose, while the bulk polymer includes a thiophene/boronic acid-substituted thiophene copolymer.

Polythiophene is a preferred polymer due in part to the ease of formation and precise control permitted by electrodeposition techniques. Also, the bulk polymer, once electrodeposited, has fairly good rigidity, which improves selectivity of the templated polymer for the analyte. Other polymers with ease of deposition and/or bulk rigidity would include polyaniline, polypyrrole, polyacetylene, and polycarbonate, with or without boronic acid substitution. Silicone-based polymers would be preferred for biocompatibility, and, if they contained the boronic acid group, would work quite well.

The boronic acid functionality exhibits covalent bond, boroester formation with most cis-2- and 3-diols. Any molecule having such diol configuration could in principle serve as the template.

The structure of 1:4 boronic acid (substituted:nonsubstituted polythiophene) is as shown below:

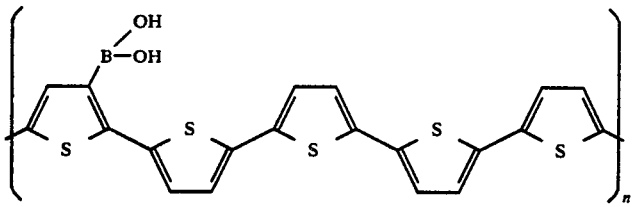

As shown, the polymeric linkage is through the 2-position, while the boronic acid group is on the 3-position. However, although this is the preferred configuration, the reverse configuration may also be used in the practice of the invention, as well as a mixture of the two configurations.

The ratio of derivatized vs. non-derivatized thiophene monomer units would be varied according to the desired parameters of the switch. The tradeoffs are structural integrity and selectivity vs. detection limit. This would be empirically determined for the particular application. However, such determination is not considered to constitute undue experimentation.

Any carboxylic acid group could be used in place of the boronic acid. These react with amine on the templating molecule with acid-base chemistry. Alternatively, the amines could be in the templated receptor site with the analyte having the carboxyl functionality.

Possible applications of an amine-containing polymer switch would be in automated vat-process control such as malic acid detection in wine-making, or control of bacterial production (e.g., commercial insulin).

Figure 1:
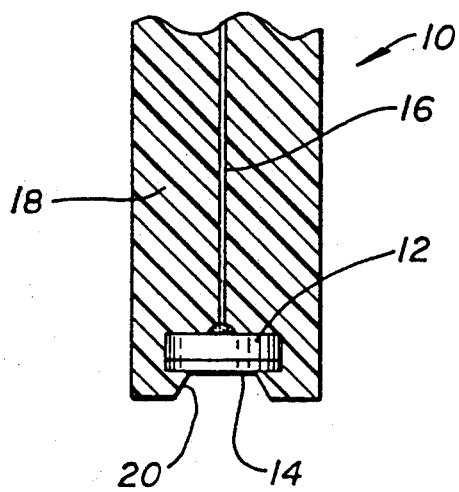
FIG. 1 depicts a cross-sectional view of a probe employing the switch of the invention.

One possible construction of the switch of the invention is depicted in FIG. 1. There, the switch 10 comprises a conductive substrate 12 on which a coating 14 of the glucose-templated polymer is formed. The substrate 12 may comprise any commonly-employed conducting material, such as a metal, e.g., copper, silver, platinum, etc., or non-metallic conductor, such as indium tin oxide.

The polymer coating 14 is formed on one side of the conducting substrate 12, while a conductive wire 16 contacts another part of the conductive substrate. The conductive wire 16 may be attached by any conventional means, such as soldering, welding, and the like.

The entire assembly is enclosed in a cylinder or tube 18 of a chemically impervious material, such as polyvinyl chloride or glass, in which an opening 20 has been formed to expose a portion of the polymer coating 14.

Where bio-compatibility is desired, the appropriate choice of materials may be made for the conductive substrate 12, the conductive wire 16, and the encasement material 18.

Figure 2:
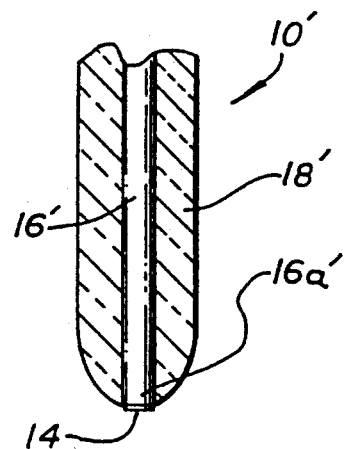
FIG. 2 depicts a cross-sectional view of an alternate probe employing the switch of the invention.

FIG. 2 depicts an alternate construction of the switch 10'. Here, a conducting wire 16', perhaps somewhat thicker than that shown in FIG. 1, is embedded, or sealed, in a soft glass capillary tube 18'. The tip 16a', of the wire 16' is exposed, such as by cutting or etching away a portion of the glass capillary tube 18', and coated with the templated polymer 14.

FIG. 3a shows the decrease in measured current as analyte concentration is increased from $10^{-6}$M (Curve 22) to $10^{-5}$M (Curve 24) to $10^{-4}$M (Curve 26) to 0.0060M (Curve 28) to 0.05M (Curve 30). The current is seen to be "off" when the analyte concentration is 0.05M.

For the electrode giving the results in FIG. 3a, the detection range for glucose is 0.036 mg/dL to 900 mg/dL. Since human blood glucose range is 30 mg/dL to about 500 mg/dL, this electrode has adequate sensitivity, detection limit, and range to function as a human blood glucose detector through the entire physiologic range. Detection range can be adjusted up, down, or both, by changing the number of receptor sites on the bulk polymer, and by changing the rigidity or depth of the polymer.

At the low end of the detection limit, for purposes of human blood glucose, or glucose levels in bacterial feed systems, there are two orders of magnitude greater sensitivity than necessary to detect the lowest possible concentration in a still-living organism ($\approx$30 mg/dL vs. 0.039 mg/dL).

Figure 3B:
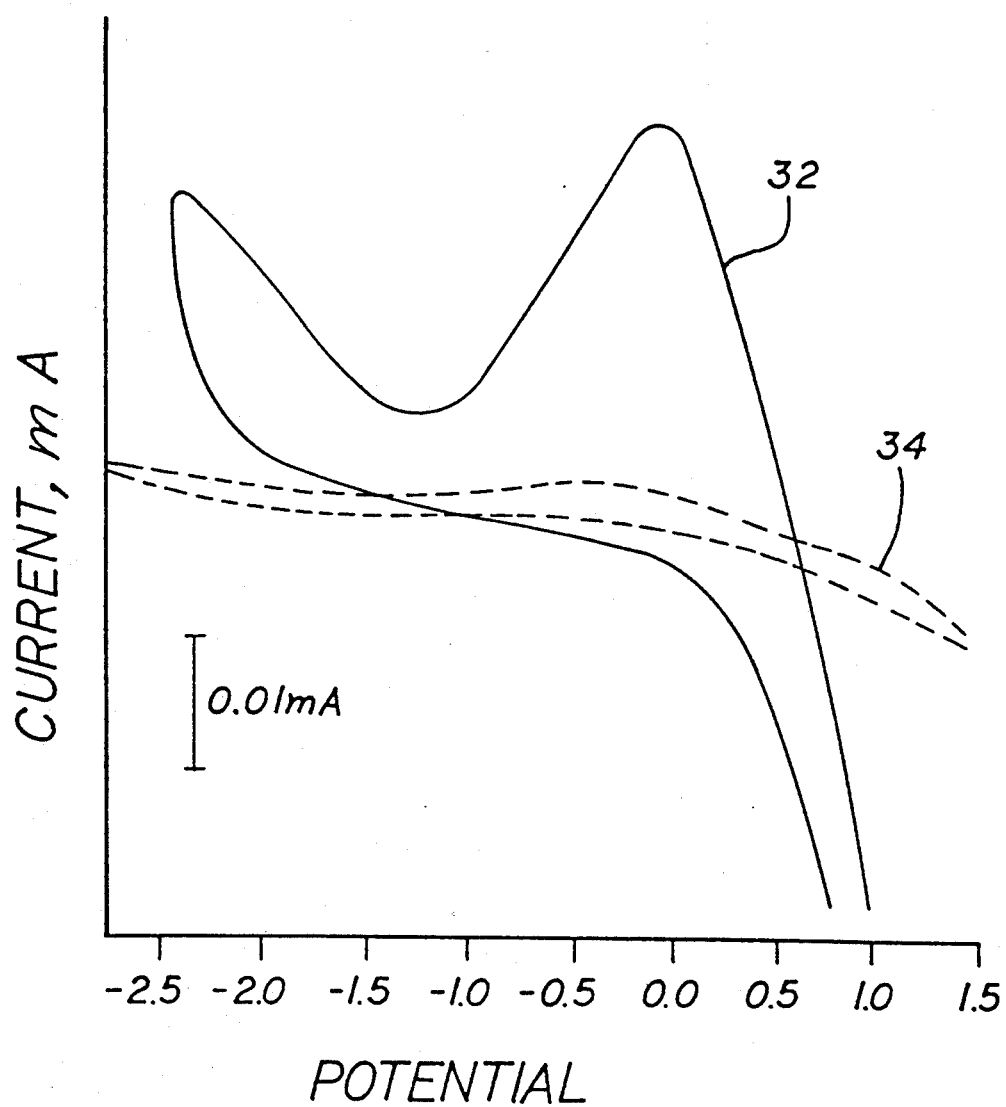
FIG. 3b, on coordinates of current and voltage, depicts the cyclic voltammetric behavior of the polymer film of FIG. 3a, without the analyte; a bare platinum electrode with no polymer coating is provided for comparison.

FIG. 3b depicts the cyclic voltammetric behavior of the polymer film of FIG. 3a. Curve 32 depicts the behavior in the absence of the analyte. Curve 34 is for a bare platinum electrode with no polymer coating, for comparison. This FIGURE shows that the polymer coating is the source of the change in behavior.

The current across this device at the activating voltage is inversely proportional to the amount of glucose in a solution in which the electrode is immersed. FIG. 3a shows the current-voltage relationship. Low concentrations of analyte (i.e., glucose) reduce the current very little, and higher concentrations, up to 0.05 moles/liter of glucose, reduce the current to the background limit. However, by modifying the polymer coating, its thickness, the number of templated sites, or its rigidity, this range may be extended.

Thus, the switch of the invention may be activated or inactivated by the concentration of glucose in a solution with which it is in contact. Advantageously, the dimensions of the switch may be very small, on the order of micrometers or less.

The glucose-templated polymer is coated onto any substrate. Conductive leads are attached in contact with the polymer, directly if the polymer is formed on an insulating or semi-insulating substrate or indirectly if the polymer is formed on a conducting substrate (as shown in FIGS. 1 and 2). The device is built into a current measuring circuit of any desired design, one of which is described in connection with FIG. 4. Since current is linearly related to the concentration of the analyte, a linear voltage relationship also obtains, when the current is dropped across a resistor.

The open circuit condition (switch off) can be set for any desired level of analyte concentration, as described more fully below with reference to FIG. 4. Closed circuit (switch on) exists at all concentrations below this point.

The switch of the invention can be used in any flowing stream or vat-type processes to activate a warning, a glucose-feed mechanism, or any other correlated device.

A miniaturized device could be used to activate an insulin release mechanism in a living organism, thus becoming an artificial beta cell such as those in the pancreas.

Figure 4:
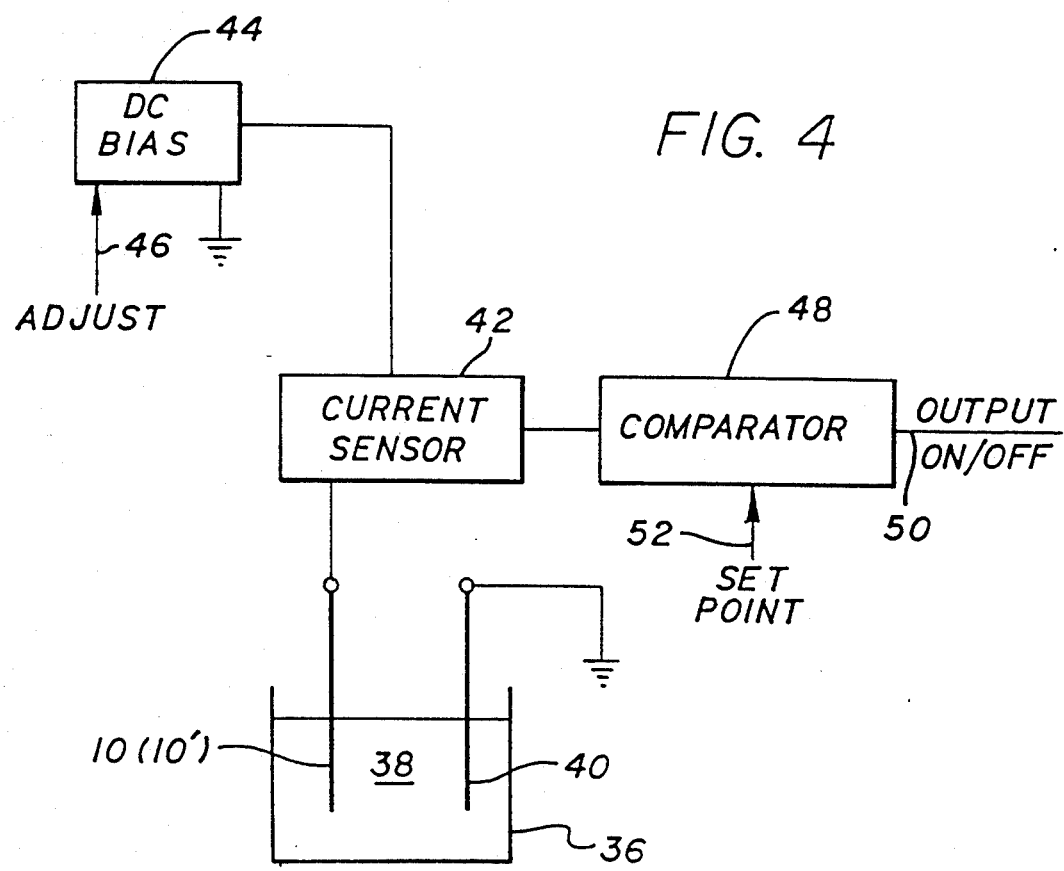
FIG. 4 depicts a circuit using the switch of the invention.

A working cell 36 is depicted in FIG. 4, with electrolyte solution 38, which could be used as an in vivo fluid, such as the human blood stream, or alternatively, interstitial fluid, cerebrospinal fluid, or subcutaneous fluid. Any fluid within a living organism in which the main constituent was water, and in which electrolytes were present (all fluids named above, for example) would function as the electrolyte solution.

To simplify design, and because this is a well-defined system, there are only two electrodes in the electrolyte solution 38. They are the working electrode 10 (or 10'), which is in this application, the glucose-templated surface, and the counter/reference electrode 40, which has two functions. The functions of this second electrode 40 are (1) to maintain the pre-set potential condition, and (2) to complete the measurement circuit in the fluid.

A current sensor 42, powered by DC bias means 44 having adjustment means 46, monitors the level of current passed between the working electrode 10 (or 10') and the counter/reference electrode 40. At zero current, comparator 48 may be in either the on or the off position, depending on the intended use of the device 36. As the current increases, it reaches a pre-set threshold and alters the state of the comparator 48. If "on" at zero current, it will shut off at the threshold value, and vice versa. As part of an automatic insulin release mechanism (not shown), it could be set in either condition, depending on the exact configuration of the circuitry of the release mechanism. Like any other switch, the device can be used to turn something on or off, either way, at the output 50.

The exact values for the circuit 36 would have to be established empirically, but the potential set at DC bias might range from about +0.6 to −0.6 volt vs. Ag-/Ag$^+$, and the amperage through the circuit would range from 0 to about 0.05 mA. The empirical establishment of the exact values is not considered to constituted undue experimentation, in view of the teachings herein. The glucose concentration cutoff threshold can be set electronically by set point means 52 for any value within the detectable range by the choice of the set threshold value on the comparator 44.

INDUSTRIAL APPLICABILITY

The analyte-activated switching device of the invention is expected to find a multitude of uses, depending on the particular analyte/polymer combination. The glucose/thiophenyl boronic acid combination may be used to monitor glucose levels, for example, in various systems, including living organisms. The detection limit, range, and sensitivity are all compatible with human blood glucose detection, as discussed above.

EXAMPLES

Example 1

Preparation of Thiophenyl Boronic Acid

Thiophenylboronic acid is unavailable commercially, and has to be prepared in the laboratory. Magnesium turnings (0.7 g) were placed in a 250 ml round bottom flask equipped with a magnetic stirrer and a reflux condenser. A mixture of 4.25 g 2-bromo thiophene in 100 ml diethyl ether was slowly added dropwise. The resulting Grignard product was filtered into a dropping funnel and slowly added dropwise into a stirred solution of 6.85 ml trimethyl borate in 100 ml dry diethyl ether at −70° C. After the mixture had stirred overnight, 10 ml distilled water was added. After a few minutes, a white precipitate was obtained. The yellow ether solution was then decanted and the ether was removed. To the brownish sediment was added 10 ml distilled water. The mixture was refluxed for 2 hrs. The hot solution was filtered. The resulting precipitate was recrystallized from hot water.

The melting range of the resulting crystals was 122° to 125° C.

Infrared analysis showed major IR absorption bands at: 3300 cm$^{-1}$, broad (due to O-H); 1560 cm$^{-1}$, sharp (due to C-C); 1440 cm$^{-1}$, sharp (due to C-H); 1380 cm$^{-1}$, medium (due to C-S); 1195 cm$^{-1}$, sharp (due to B-C); 1100 cm$^{-1}$, strong (due to B-O).

The nuclear magnetic resonance spectrum obtained in deuterated DMSO contained peaks at: $\delta$ 7.70, 1H (a triplet due to the proton with two neighbors on the thiophene ring); $\delta$ 8.26, 2H (due to the other protons on the thiophene ring); $\delta$ 8.86 2H (due to the O-H protons).

Example 2

Templating of Thiophenyl Boronic Acid

Thiophenyl boronic acid (0.290 g) from Example 1 was placed in a clean mortar and 2.20 g of D-glucose was added. The solids were crushed together until a fine powder was obtained. This powder was warmed very gently until it melted. The temperature was maintained at the melting point for 5 minutes. The melt was then extracted with petroleum ether. The ether was removed from the extract, and an IR spectrum was obtained of the residue.

The major absorption bands were at 3450 cm$^{-1}$ (due to O-H); 2975 cm$^{-1}$ (due to C-H); 1540 cm$^{-1}$ (due to C-C); 1450 cm$^{-1}$ (due to C-H); 1380 cm$^{-1}$ (due to C-S); and 1210 cm$^{-1}$ (due to B-O). The widths were substantially as observed above. This spectrum was different from both the glucose and thiophenyl boronic acid spectra, and is consistent with dithiophenyl boronic ester of glucose, probably in the furanose form.

Example 3

Electrodeposition of the Templated Polymer

A standard solution of 0.376M thiophene and 0.519M lithium tetrafluoroborate was prepared in acetonitrile. Glucose-complexed thiophenyl boronic acid (0.0020 g) from Example 2 was placed in a clean 1 ml beaker, and 1 ml of the standard thiophene solution was added. This provided approximately 6% by weight of the templating agent to underivatized thiophene in the solution. The beaker was fitted with a lid into which were inserted a platinum wire working electrode, a platinum counter electrode, and a saturated Ag/AgCl reference electrode. A PAR potentiostat was used to provide the controlled current of 412 μA for 30 seconds, while stirring the solution. A continuous, green film appeared on the electrode, which was shown to be different from thiophene alone by STM (scanning tunneling microscopy), ATR-FTIR (attenuated total reflectance - Fourier transform infra-red spectroscopy), and electrochemical means. The data were all consistent with the glucose incorporated into the polymer via boronic ester formation.

Example 4

Removal of Templating Glucose from Polymer Matrix

The working electrode prepared in Example 3 was removed from the plating solution and rinsed with acetonitrile to remove any non-bonded material. It was then heated gently in a pH 4 solution for about 30 minutes. Analysis of the solution after removal of the electrode showed a concentration of glucose appropriate to the calculated surface coverage of the electrode. The electrode was now ready for use in glucose determinations.

INDUSTRIAL APPLICABILITY

The switching device of the invention is expected to find use in determining the level of, for example, glucose.

Thus, there has been disclosed a switching device adapted to detect the concentration level of a templated molecule, such as glucose. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A switching device having a preset open circuit condition for a given analyte concentration, comprising a micro-electrode coated with a polymer contacted by a conductive lead, said polymer having templated sites for accepting analyte molecules, each templated site comprising a vacancy in said polymer that is selective for said analyte molecule.

2. The switching device of claim 1 wherein said analyte is selected from the group consisting of cis-2-diols and cis-3-diols.

3. The switching device of claim 2, wherein said analyte comprises glucose.

4. The switching device of claim 1 wherein said polymer is selected from the group consisting of thiophene/-boronic acid-substituted thiophene copolymer; aniline/-boronic acid-substituted aniline copolymer; pyrrole/boronic acid-substituted pyrrole copolymer; acetylene/-boronic acid-substituted acetylene copolymer; carbonate/boronic acid-substituted carbonate copolymer; boronic acid-substituted silicon-based polymers, and copolymers thereof.

5. The switching device of claim 1 wherein said analyte consists essentially of glucose and said polymer consists essentially of thiophene/boronic acid-substituted thiophene copolymer.

6. A switching device having a preset open circuit condition for a given glucose concentration, comprising a micro-electrode coated with thiophene/boronic acid-substituted thiophene copolymer contacted by conductive leads, said copolymer having templated sites for accepting glucose molecules.

* * * * *